(12) United States Patent
White et al.

(10) Patent No.: US 11,000,321 B2
(45) Date of Patent: May 11, 2021

(54) SECONDARY SCREW BLOCKING MECHANISM

(71) Applicant: Altus Partners LLC, West Chester, PA (US)

(72) Inventors: Patrick M. White, Avondale, PA (US); Brian R. Bankoski, Avondale, NJ (US); Michael Fitzgerald, Newtown Square, NJ (US); Randy Davis, Glen Burnie, MD (US)

(73) Assignee: ALTUS PARTNERS LLC, West Chester, PA (US)

( * ) Notice: Subject to any disclaimer, the term of this patent is extended or adjusted under 35 U.S.C. 154(b) by 404 days.

(21) Appl. No.: 15/801,462

(22) Filed: Nov. 2, 2017

(65) Prior Publication Data

US 2018/0338785 A1 Nov. 29, 2018

Related U.S. Application Data

(60) Provisional application No. 62/510,902, filed on May 25, 2017.

(51) Int. Cl.
| | |
|---|---|
| *A61B 17/80* | (2006.01) |
| *A61B 17/70* | (2006.01) |
| *A61F 2/30* | (2006.01) |
| *A61F 2/44* | (2006.01) |

(Continued)

(52) U.S. Cl.
CPC ...... *A61B 17/8042* (2013.01); *A61B 17/7059* (2013.01); *A61B 17/8047* (2013.01); *A61F 2/30771* (2013.01); *A61B 17/86* (2013.01); *A61B 2017/564* (2013.01); *A61F 2/30749* (2013.01); *A61F 2/447* (2013.01); *A61F 2002/30405* (2013.01); *A61F 2002/30507* (2013.01); *A61F 2002/30528* (2013.01); *A61F 2002/30787* (2013.01)

(58) Field of Classification Search
CPC ............ A61B 17/8033; A61B 17/8038; A61B 17/8042; A61B 17/8047; A61B 17/7059; A61F 2/30771
See application file for complete search history.

(56) References Cited

U.S. PATENT DOCUMENTS

| | | |
|---|---|---|
| 5,261,910 A | 11/1993 | Warden |
| 5,364,399 A | 11/1994 | Lowery |
| 5,423,826 A | 6/1995 | Coates |

(Continued)

FOREIGN PATENT DOCUMENTS

WO 2005/011508 A1 2/2005

OTHER PUBLICATIONS

Neurosurg Focus 12 (1): Article 15, 2002, "The Cervical Spine Study Group anterior cervical plate nomenclature" by Regis W. Hain, M.D., et al., Department of Neurosurgery, 7 pages.

*Primary Examiner* — Si Ming Ku
(74) *Attorney, Agent, or Firm* — Matthew B. Dernier, Esq.

(57) ABSTRACT

Methods and apparatus provide for an orthopedic device, including: a base element having a plurality of apertures extending therethrough for receiving a respective bone fixation element; a retaining mechanism operating to prevent withdrawal of the fixation element; and a blocker operating to overlie the bone fixation element within the one of the apertures such that the bone fixation element is prevented from withdrawing from one or more bones of the patient.

18 Claims, 7 Drawing Sheets

(51) Int. Cl.
*A61B 17/56* (2006.01)
*A61B 17/86* (2006.01)

(56) References Cited

U.S. PATENT DOCUMENTS

| | | |
|---|---|---|
| 5,549,612 A | 8/1996 | Yapp |
| 6,139,550 A | 10/2000 | Michelson |
| 6,258,089 B1 | 7/2001 | Campbell et al. |
| 6,261,291 B1 | 7/2001 | Talaber et al. |
| 6,306,139 B1 | 10/2001 | Fuentes |
| 6,361,537 B1 | 3/2002 | Anderson |
| 6,599,290 B2 | 7/2003 | Bailey et al. |
| 6,602,255 B1 | 8/2003 | Campbell et al. |
| 6,626,907 B2 | 9/2003 | Campbell et al. |
| 6,755,833 B1 | 6/2004 | Paul et al. |
| 7,025,769 B1 | 4/2006 | Ferree |
| 7,306,605 B2 | 12/2007 | Ross |
| 7,318,825 B2 | 1/2008 | Butler et al. |
| 7,481,811 B2 | 1/2009 | Suh |
| 8,906,077 B2 | 12/2014 | Bush, Jr. |
| 2004/0087951 A1 | 5/2004 | Khalili |
| 2004/0153069 A1 | 8/2004 | Paul |
| 2005/0010227 A1 | 1/2005 | Paul |
| 2005/0021032 A1 | 1/2005 | Koo |
| 2006/0229620 A1 | 10/2006 | Rothman |
| 2018/0103989 A1* | 4/2018 | Altarac ............. A61B 17/7059 |

\* cited by examiner

SECONDARY SCREW BLOCKING MECHANISM

CROSS REFERENCE TO RELATED APPLICATIONS

This application claims the benefit of U.S. Provisional Patent Application No. 62/510,902, filed May 25, 2017, the entire disclosure of which is hereby incorporated by reference.

BACKGROUND

The present invention relates to the surgical field of orthopedics and providing an additional safety aspect to orthopedic implants to further ensure patient safety. For example, the present invention is directed to a bone fastener retainer for orthopedic implants, such as spinal plates, spinal cages, etc.

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on health care expenditures.

Degenerative spinal column diseases, such as disc degenerative diseases (DDD), spinal stenosis, spondylolisthesis, and so on, need surgical operation if they do not take a turn for the better by conservative management. Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Conventional methods of spinal fixation utilize a rigid orthopedic device to support an injured spinal part and prevent movement of the injured part. Among these conventional orthopedic devices (often referred to as spinal fixation devices) are cervical plates, cervical stand-alone cages, lateral lumbar plates, stand-alone lumbar anterior cages, etc.

An accepted procedure for treating spinal disorders involves using an orthopedic device, such as the aforementioned types, to hold vertebrae in desired spatial relationships and orientations relative to each other. The patient's spine can be approached anteriorly or posteriorly, and in either case, holes are drilled (and often tapped) in at least two adjacent vertebrae, which holes are accurately positioned with reference to openings formed through the orthopedic device. Screws or other fasteners are used to secure the orthopedic device to the vertebrae. In some cases the screws may be self-tapping.

One of the problems associated with the aforementioned technique is the tendency of the bone screws or other fasteners to gradually work loose after implantation. Slight shock or vibration of the vertebrae over time, due to walking, climbing stairs or more vigorous activity by the patient following treatment increases this tendency, jeopardizing the integrity of the fixation via the orthopedic device. Moreover, as the fasteners work loose, the outward protrusion of the heads over other components of the orthopedic device can be a source of discomfort and present the risk of trauma to adjacent and surrounding soft tissue.

There have been attempts to solve the above problem. Indeed, there are requirements to employ a blocking mechanism in connection with the orthopedic device to ensure that bone fixation screws do not back out of the device while in-situ. In particular it has become a standard requirement to have a blocking means in most cervical plates, cervical stand-alone cages, lateral lumbar plates and stand-alone lumbar anterior cages that use bone screws for fixation.

Several popular product designs are shown in U.S. Pat. No. 6,139,550, the entire disclosure of which is incorporated herein by reference. The devices disclosed in U.S. Pat. No. 6,139,550 generally entail the use of a rotary activated screw head or cam plate blocker to cover the head of the bone fixation screws. Depending on design and tolerance these devices may provide some measure of usefulness; however there has been discussion about the need for some assurance that the disclosed blockers themselves do not loosen and rotate while in-situ.

As conventional devices for screw retention have not provided a comprehensive solution to the tendency of the bone screws (and blockers) to work loose in-situ, there is a need for a secondary blocking mechanism to ensure that the blocker does not itself loosen in-situ.

SUMMARY OF THE DISCLOSURE

In accordance with one or more embodiments, methods and/or apparatus provide for an orthopedic device, comprising: a base element having a primary surface, and a plurality of apertures extending from the primary surface through the base element, each aperture for receiving a respective bone fixation element that is driven into one or more bones of a patient in order to couple the orthopedic device to the patient; and a retaining mechanism operating to interrupt at least one of the fixation elements from withdrawing from the one or more bones of the patient.

The retaining mechanism includes: a threaded bore extending from the primary surface into the base element, and being located adjacent to at least one of the apertures; a detent feature disposed on, and extending outward from, the primary surface of the base element proximate to the threaded bore, and located adjacent to a periphery of the at least one of the apertures; and a blocker having a threaded shaft engaging the threaded bore, and a head at one end of the threaded shaft.

Rotation of the blocker causes the head to overlie at least one bone fixation element within the at least one of the apertures such that the at least one bone fixation element is prevented from withdrawing from the one or more bones of the patient. The rotation of the blocker also drives the head into engagement with the detent feature in such a way that counter rotation of the blocker sufficient to release the head from overlying the at least one bone fixation element is inhibited.

The detent feature includes an upper surface spaced away from, directed away from, and oriented substantially parallel to, the primary surface of the base element. The head of the blocker includes a contact surface oriented towards, and substantially parallel to, the primary surface of the base element. Rotation of the blocker drives the contact surface of the head of the blocker into engagement with the upper surface of the detent feature.

The extension of the detent feature outward from the primary surface of the base element defines a first sidewall oriented transversely with respect to the primary surface of the base element, where the first sidewall is located adjacent to the periphery of the at least one of the apertures. The head of the blocker includes a second sidewall oriented transversely with respect to the primary surface of the base element. Initial rotation of the blocker drives the contact surface of the head of the blocker into engagement with the upper surface of the detent feature. Further rotation of the blocker slides the contact surface rotationally across, and into tighter engagement with, the upper surface of the detent feature thereby taking up slack in the threaded shaft within the threaded bore.

Further subsequent rotation of the blocker slides the contact surface off of the upper surface of the detent feature such that the first sidewall of the detent feature and the second sidewall of the blocker are oriented in opposition to one another. The further subsequent rotation of the blocker results in a portion of the head of the blocker to overly the at least one of the apertures, thereby preventing the at least one of the bone fixation elements from withdrawing from the one or more bones of the patient.

Other aspects, features, and advantages of the present invention will be apparent to one skilled in the art from the description herein taken in conjunction with the accompanying drawings.

BRIEF DESCRIPTION OF DRAWINGS

For the purposes of illustration, there are forms shown in the drawings that are presently preferred, it being understood, however, that the invention is not limited to the precise arrangements and instrumentalities shown.

DETAILED DESCRIPTION

Figure 1:
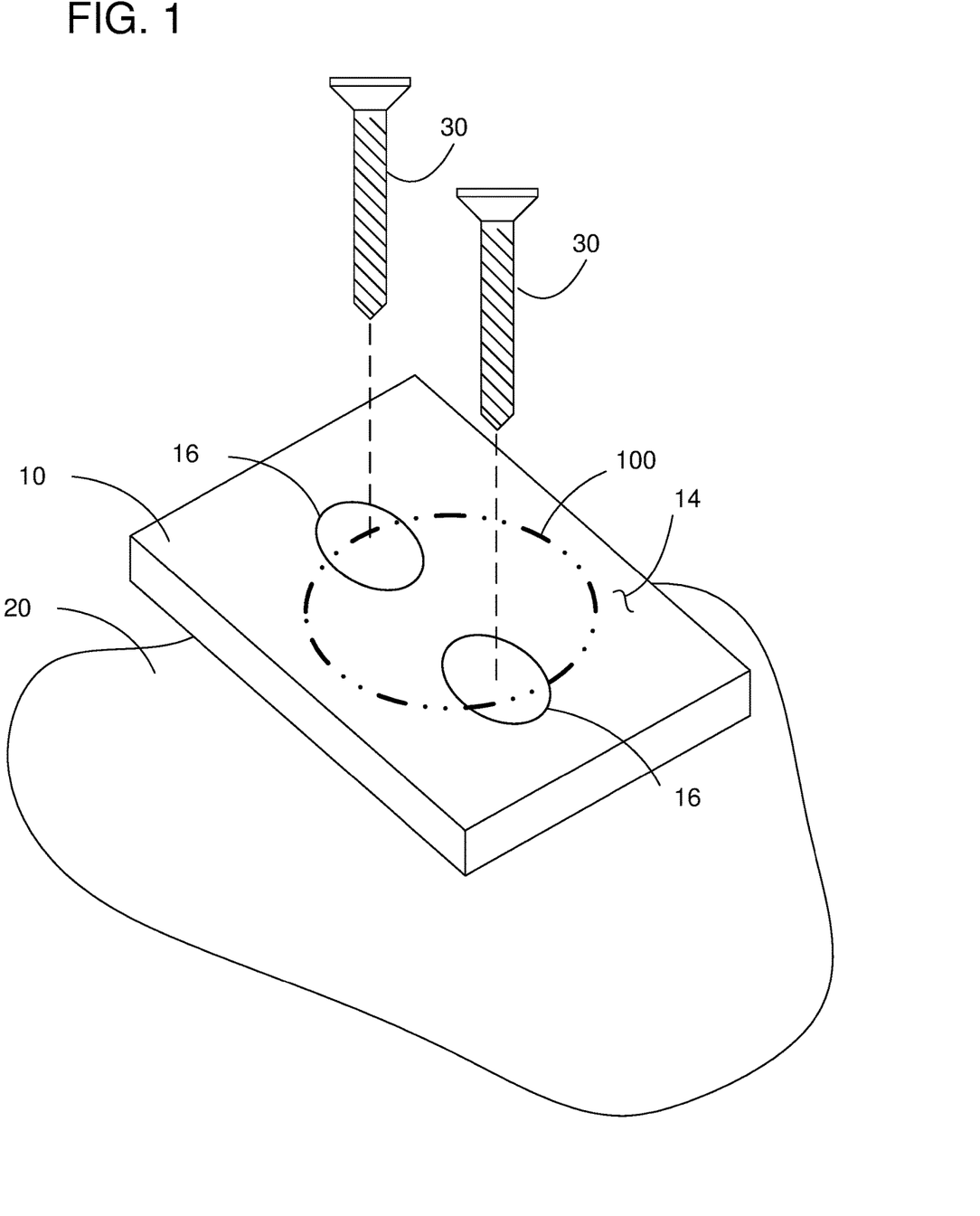
FIG. 1 is a perspective, schematic view of an orthopedic device in accordance with embodiments of the present invention.

With reference to the drawings wherein like numerals indicate like elements there is shown in FIG. 1 a schematic representation of an orthopedic device 10, such as a spinal plate, a spinal cage, etc. Although the detailed embodiments disclosed herein may refer to the orthopedic device 10 in connection with treatments of the spine, other treatments are contemplated and supported herein, indeed wherever fixation of an orthopedic device 10 to one of more bones 20 of a patient via one or more bone fixation elements 30 (e.g., bone screws, anchors, fasteners, etc.) is required.

As mentioned above, many protocols call for some means for preventing the bone fixation elements 30 from backing out of the one or more bones 20 of the patient after implantation. Also mentioned above is the fact that conventional devices provide some interference member overlying the bone fixation elements 30 to inhibit withdrawal thereof, yet the interference member itself is not prevented from backing out to problematic degrees. In accordance with the embodiments herein, a novel retaining mechanism 100 is disclosed which addresses the problem with the conventional devices.

Figure 2:
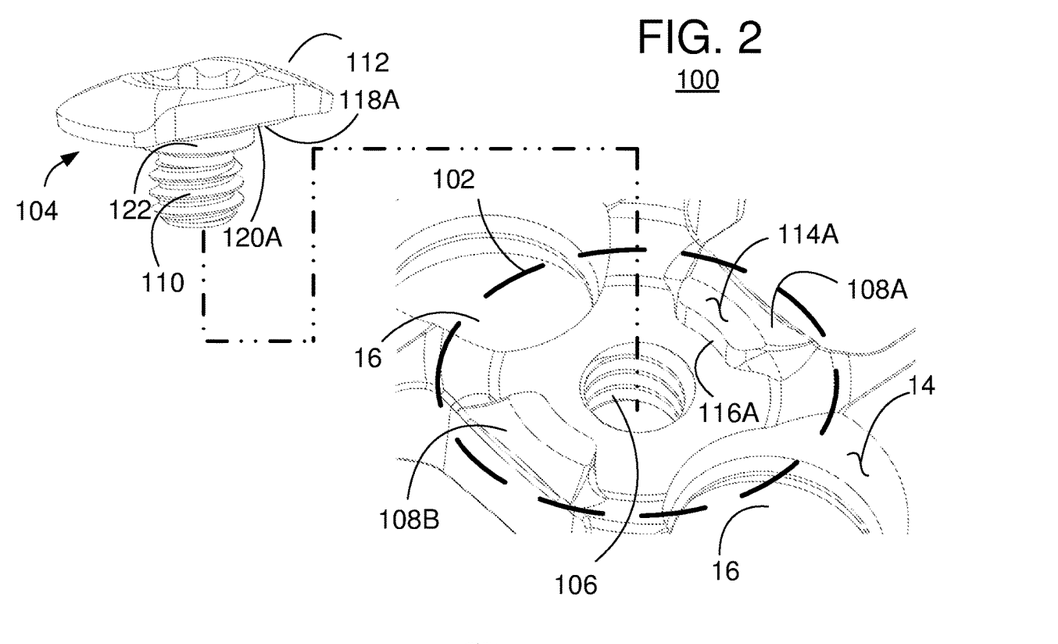
FIG. 2 is a perspective, detailed view of a retaining mechanism suitable for use in one or more embodiments disclosed herein.
Figure 3:
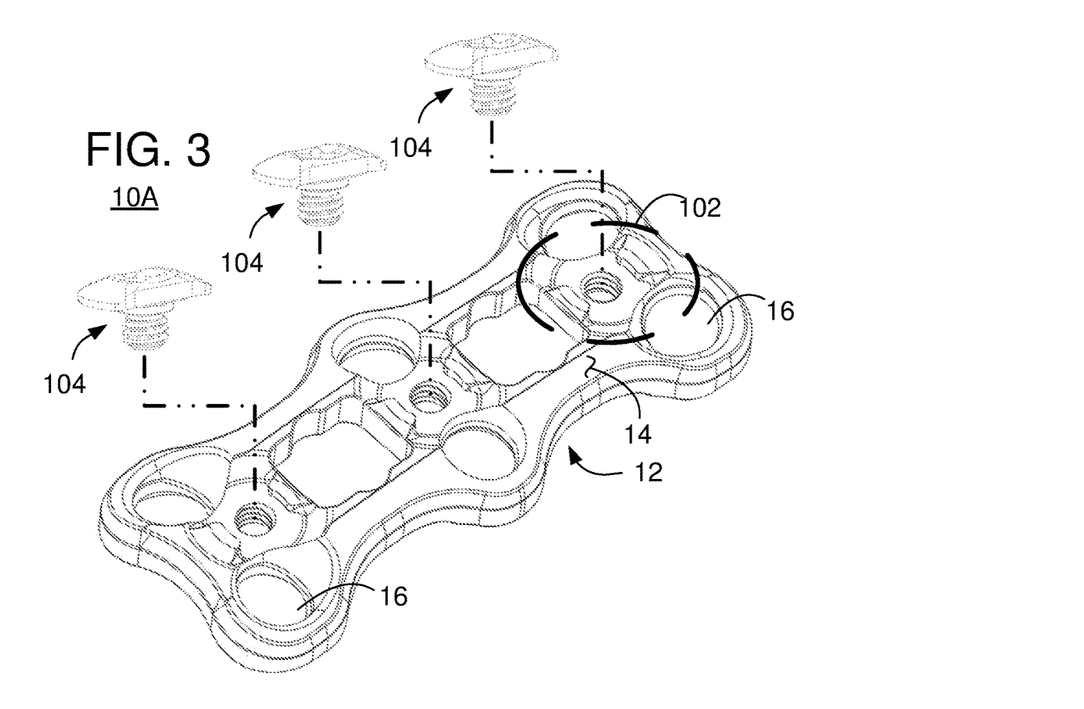
FIG. 3 is a perspective view of a particular orthopedic device, i.e., a spinal plate, employing three of the retaining mechanisms.

With reference to FIGS. 2-3, the retaining mechanism 100 includes a number of features, which are distinguishable over conventional devices. In order to provide some context, the disclosed example includes an orthopedic device 10 used to treat spinal disorders, specifically a spinal plate 10A. As is known in the art, the orthopedic device 10A includes a base element 12 (in this case the main body of the spinal plate 10A) having a primary surface 14, and a plurality of apertures 16 extending from the primary surface 14 through the base element 12. Each aperture 16 is sized and shaped to receive a respective bone fixation element 30 (such as a bone screw, anchor, fastener, etc.) that is driven into one or more bones 20 of the patient in order to couple the orthopedic device 10A to the skeletal structure of the patient.

Details of the retaining mechanism 100 are shown in FIG. 2, where the retaining mechanism 100 operates to interrupt at least one of the bone fixation elements 30 from withdrawing from the one or more bones 20 of the patient after implantation. In the embodiment illustrated in FIG. 2, the retaining mechanism 100 operates to interrupt two bone fixation elements 30 from withdrawing from the one or more bones 20. The retaining mechanism 100 includes two fundamental mechanisms, namely, features 102 on, or integral with, the orthopedic device 10A and a blocker element 104. In the embodiment illustrated in FIG. 3, the orthopedic device 10A includes six apertures through which respective bone fixation elements 30 are driven into the one or more bones 20 of the patient (not shown). A respective retaining mechanism 100 (the combination of features 102 and blocker element 104) is disposed proximate to each laterally adjacent pair of apertures 16.

Among the features 102 of the retaining mechanism 100 on, or integral with, the orthopedic device 10A is a threaded bore 106 extending from the primary surface 14 into the base element 12, and the threaded bore 106 is located adjacent to at least one of the apertures 16. Again, in the illustrated embodiment, there are a pair of adjacent apertures 16 and the threaded bore 106 is located between the pair, i.e., adjacent to both of the adjacent apertures 16.

The features 102 of the retaining mechanism 100 also include at least one detent feature 108 disposed on, and extending outward from, the primary surface 14 of the base element 12. The at least one detent feature 108 is disposed proximate to the threaded bore 106 (e.g., proximate to a periphery thereof) and adjacent to at least one of the apertures 16. In the illustrated embodiment, the at least one detent feature 108 includes a first detent feature 108A and a second detent feature 108B, each being disposed on, and extending outward from, the primary surface 14 of the base element 12 and proximate to the threaded bore 106. More specifically, the first detent feature 108A is located on one side of the threaded bore 106 and the second detent feature 108B is disposed on an opposite side of the threaded bore 106 from the first detent feature 108A.

The blocker 104 includes a threaded shaft 110 having thread characteristics suitable to threadingly engage the threaded bore 106. The blocker 104 also includes a head 112 at one end of the threaded shaft 110. Although further details will be presented below, in general, rotation of the blocker 104 causes the head 112 to overlie the at least one bone fixation element 30 within the at least one of the apertures 16 (in this example two such elements 30 in two respective apertures 16) such that the at least one bone fixation element 30 is prevented from withdrawing from the one or more bones 20 of the patient. Additionally, the rotation of the blocker 104 drives the head 112 into engagement with the detent feature 108 (in this example two such detent features 108A, 108B) in such a way that in-situ counter rotation of the blocker 104 sufficient to release the head 112 from overlying the at least one bone fixation element 30 is inhibited.

The above functionality is achieved through some specific characteristics of the features 102 and the blocker 104 of the retaining mechanism 100.

For example, the first detent feature 108A includes a (first) upper surface 114A spaced away from, directed away from, and oriented substantially parallel to, the primary surface 14 of the base element 12 of the orthopedic device 10A. Furthermore, the extension of the first detent feature 108A outward from the primary surface 14 of the base element 12 defines a first sidewall 116A (which may include sub-sidewall elements) oriented transversely with respect to the primary surface 14 of the base element 12. The first sidewall 116A is located adjacent to (and at least partially directed toward) the threaded bore 106, and is also located adjacent to the periphery of the at least one of the apertures 16 (in this example two such apertures 16).

The second detent feature 108B, includes similar elements as the first detent feature 108A. For example, the extension of the second detent feature 108B outward from the primary surface 14 of the base element 12 defines a second sidewall 116B (which may include sub-sidewall elements). The second sidewall 116B is oriented transversely with respect to the primary surface 14 of the base element 12, and oppositely from the first sidewall 116A of the first detent feature 108A, specifically on an opposite side of the threaded bore 106.

Turning now to further details of the blocker 104, the head 112 thereof includes at least one contact surface 118, such as a first contact surface 118A, which is oriented towards, and substantially parallel to, the primary surface 14 of the base element 12. In the illustrated embodiment, the head 112 includes two contact surfaces; namely, the first contact surface 118A and a second contact surface 118B, each located on opposing sides of the threaded shaft 110.

Furthermore, the head 112 of the blocker 104 includes at least one opposing sidewall 120, such as a first opposing sidewall 120A, oriented transversely with respect to the primary surface 14 of the base element 12, which is to say also transversely with respect to, and adjacent to, the at least one (e.g., the first and second) contact surfaces 118A, 118B. In the illustrated embodiment, the head 112 includes first and second opposing sidewalls 120A, 120B. The second opposing sidewall 120B is oriented transversely with respect to the primary surface 14 of the base element 12, is oriented transversely with respect to the at least one (e.g., the first and second) contact surfaces 118A, 118B, and is disposed on an opposite side of the threaded shaft 110 from the first opposing sidewall 120A.

In addition, the head 112 of the blocker 104 includes a shoulder surface, which is annularly disposed about the threaded shaft 110, particularly where the threaded shaft 110 engages the head 112.

Figure 4:
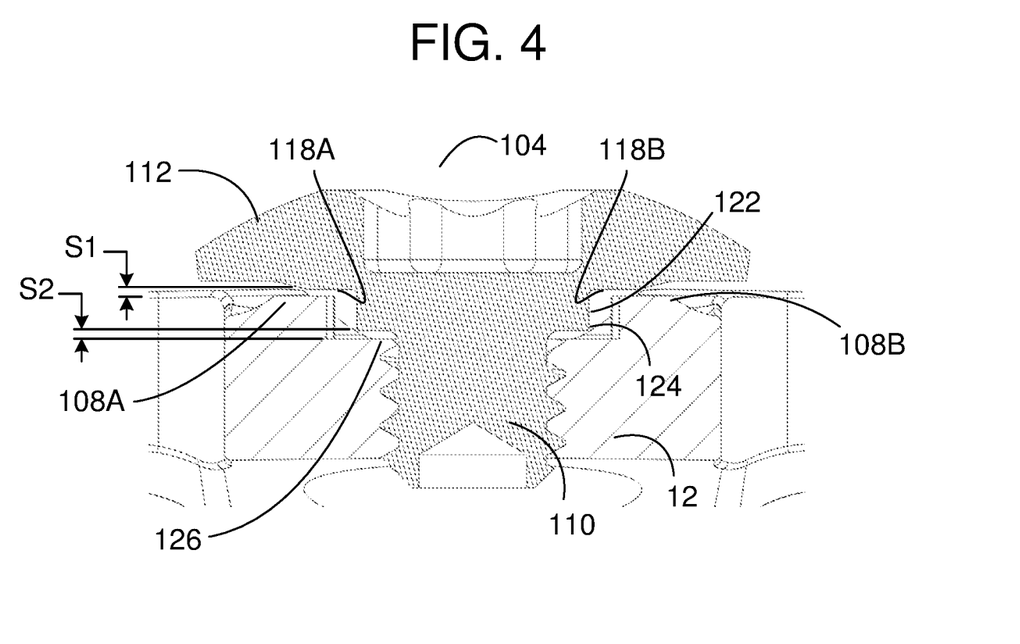
FIG. 4 is a cross sectional view of the retaining mechanism, taken through section 4-4 of FIG. 5 at a particular phase of a locking procedure.
Figure 5:
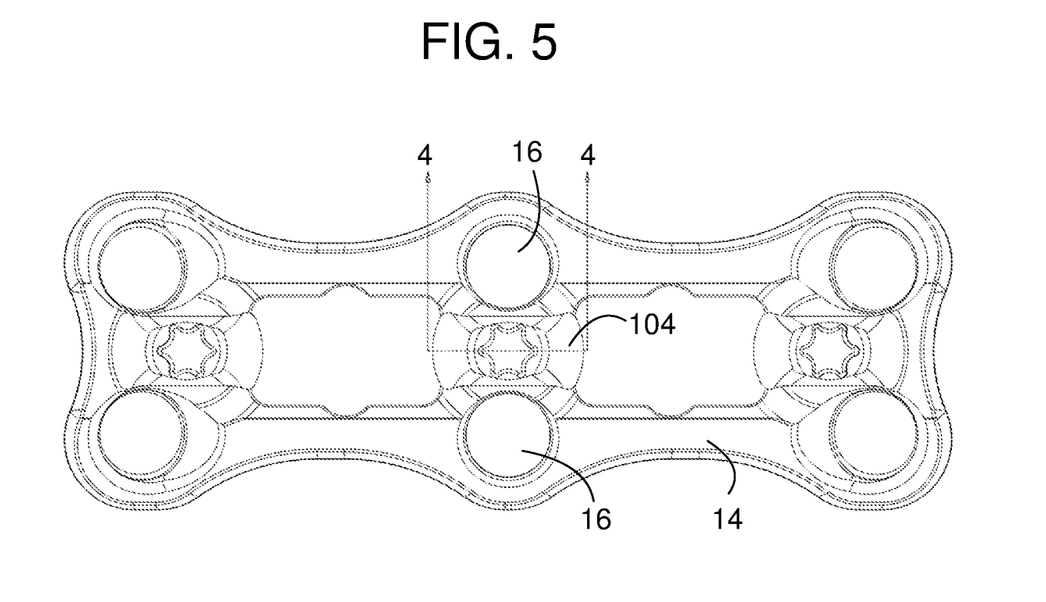
FIG. 5 is top view of the orthopedic device during the particular phase of the locking procedure of FIG. 4.

Reference is now made to FIGS. 4 and 5, which illustrate an initial phase of coupling and locking the blocker 104 to the feature 102 of the retaining mechanism 100. The threaded shaft 110 of the blocker 104 is disposed into engagement with the threaded bore 106 of the feature 102 and rotated. The blocker 104 may include a means for activating such rotation, such as a male or female drive, preferably a female drive 124, which is engaged by a complementary drive element of an insertion tool (not shown).

During the initial phase of rotation of the blocker 104, the first and second contact surfaces 118A, 118B will reach an initial spacing S1 above the first and second upper surfaces 114A, 114B of the first and second detent features 108A, 108B. Additionally, a lower peripheral edge 124 of the shoulder surface 122 will reach an initial spacing S2 from a base surface 126 of the feature 102. At this point, although not shown, the respective bone fixation elements 30 may be inserted through the respective apertures 16 of the spinal plate 10A and driven into the one or more bones 20 of the patient.

Figure 6:
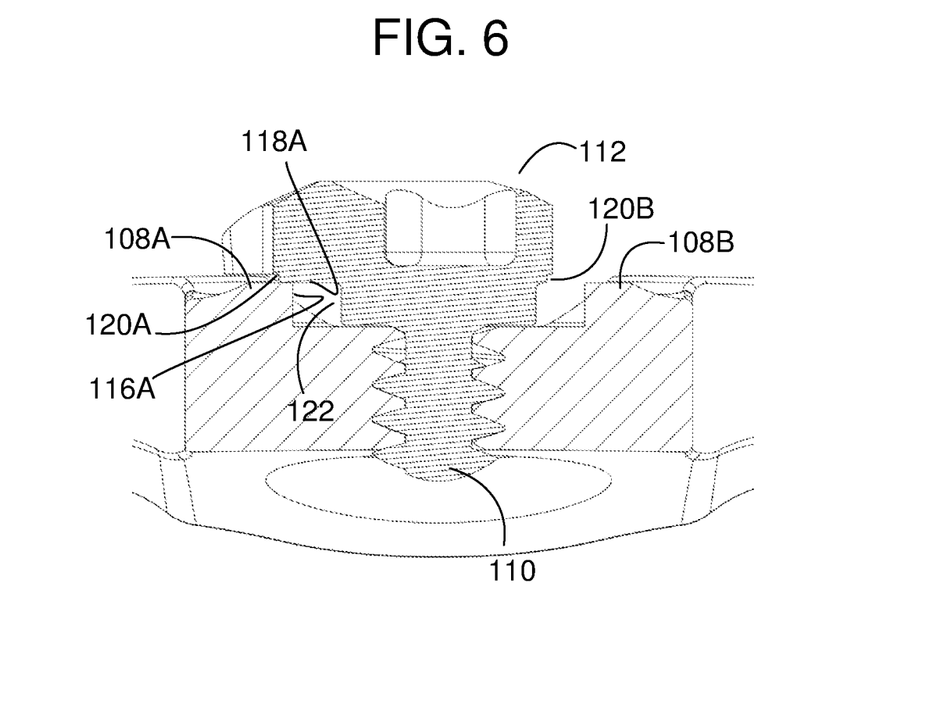
FIG. 6 is a cross sectional view of the retaining mechanism, taken through section 6-6 of FIG. 7 at a further phase of the locking procedure.
Figure 7:
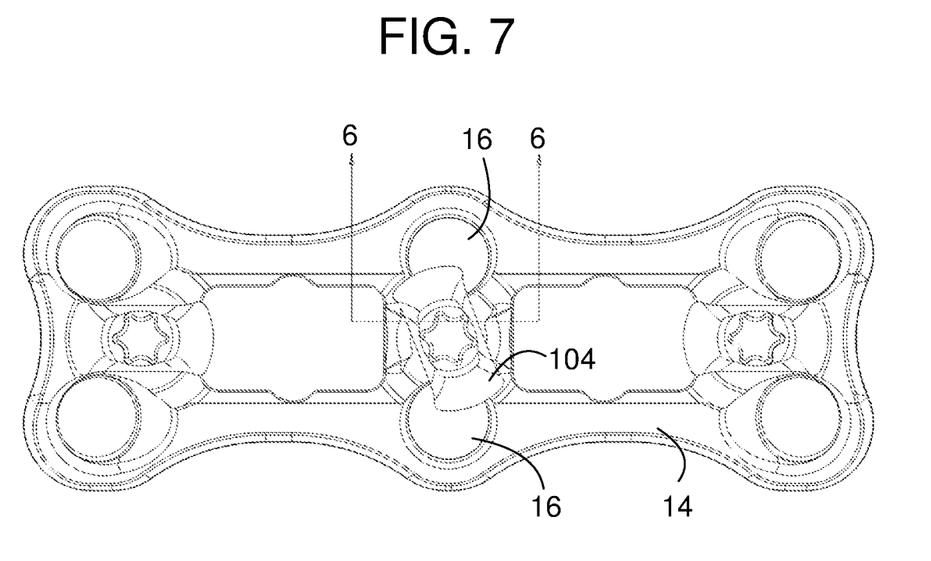
FIG. 7 is top view of the orthopedic device during the particular further phase of the locking procedure of FIG. 6.

In a next phase of locking the blocker 104 to the feature 102 of the retaining mechanism 100, the blocker 104 is further rotated to reach an intermediate position, which is illustrated in FIGS. 6 and 7. At this point in the rotation of the blocker 104, the contact surface 118 of the head 112 has been driven into engagement with the upper surface 114 of the detent feature 108. More specifically, given the particular cross section shown, the first contact surface 118A of the head 112 has been driven into engagement with the first upper surface 114A of the first detent feature 108A. Although not shown in the illustration, similar engagement would be achieved between the second contact surface 118B of the head 112 and the second upper surface 114B of the second detent feature 108B.

Further rotation of the blocker 104 slides the first and second contact surfaces 118A, 118B rotationally across, and into tighter engagement with, the respective first and second upper surfaces 114A, 114B of the first and second detent features 108A, 108B, thereby taking up any slack in the threaded shaft 110 within the threaded bore 106. Notably, at this point in the rotation, the first and second opposing sidewalls 120A, 120B remain free and unimpeded from any counter-rotations of the blocker 104.

Figure 8:
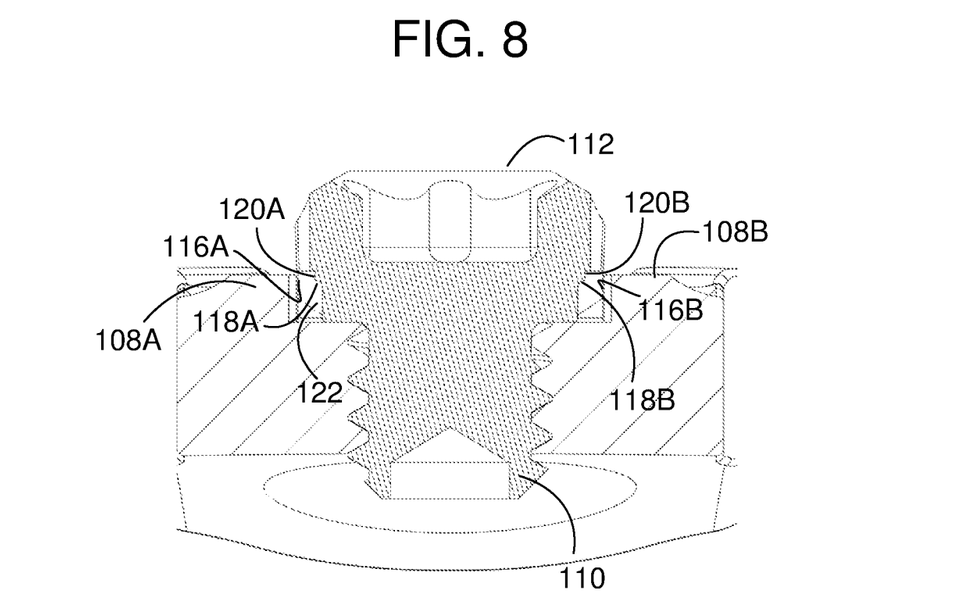
FIG. 8 is a cross sectional view of the retaining mechanism, taken through section 8-8 of FIG. 9 at a final phase of the locking procedure.
Figure 9:
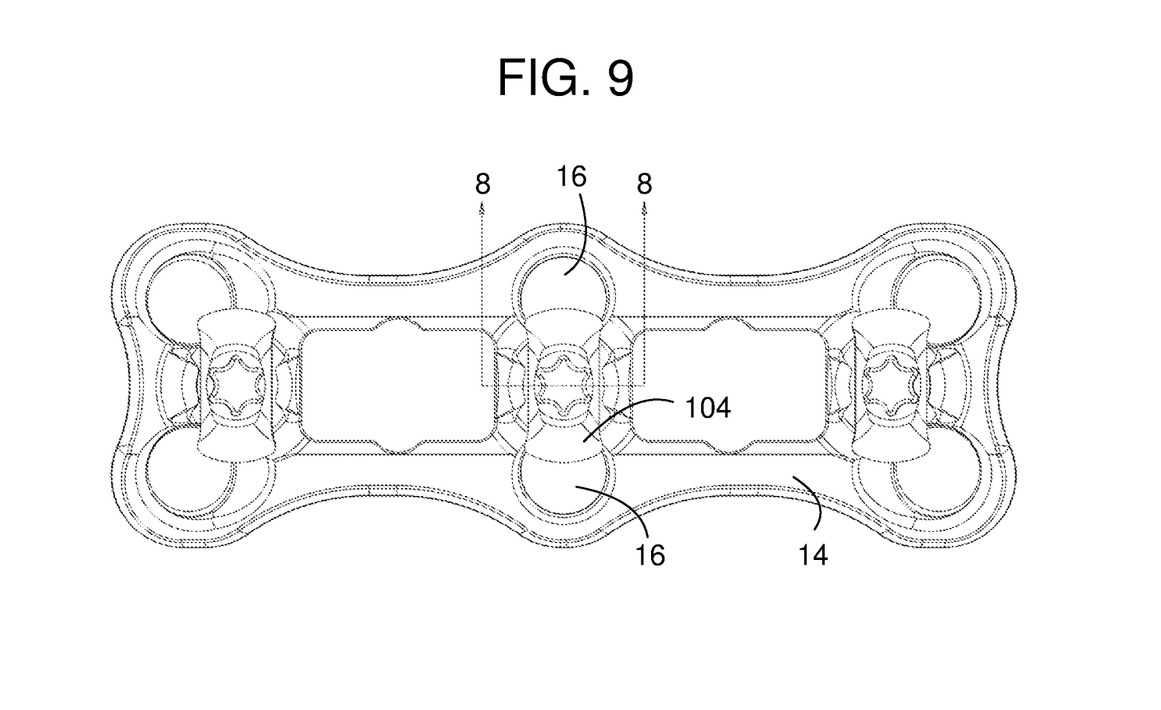
FIG. 9 is top view of the orthopedic device during the final phase of the locking procedure of FIG. 8.

Reference is now made to FIGS. 8-9, which illustrate a locked phase of the blocker 104 with respect to the feature 102 of the retaining mechanism 100. The action of further subsequent rotation of the blocker 104 (as compared with the position shown in FIGS. 6-7) causes the first contact surface 118A to slide off of the first upper surface 114A of the first detent feature 108A such that the first sidewall 116A of the first detent feature 108A and the first opposing sidewall 120A of the blocker 104 are oriented in opposition to one another. Similarly, such further subsequent rotation of the blocker 104 simultaneously causes the second contact surface 118B to slide off of the second upper surface 114B of the second detent feature 108B such that the second sidewall 116B of the second feature 108B and the second opposing sidewall 120B of the blocker 104 are oriented in opposition to one another.

As the first and second contact surfaces 118A, 118B slide off of the first and second upper surfaces 114A, 114B, a certain magnitude of torque releases tensions between respective components and allows the threads 106, 110 to loosen somewhat. The release of the torque provides the user with a positive sensation, indicating that the blocker 104 is near the locked position of FIGS. 8-9.

With the lower peripheral edge 124 of the shoulder portion 122 in engagement with the base surface of the feature 102, the blocker 30 is in a desired, and completely locked, resting position. In this position, the first and second contact surfaces 118A, 118B of the blocker 104 are below the respective first and second upper surfaces 114A, 114B of the first and second detent features 108A, 108B. Importantly, the further subsequent rotation of the blocker 104 (from the position in FIGS. 6-7 to the position in FIGS. 8-9) results in respective portions of the head 112 of the blocker 104 overlying the apertures 116, thereby preventing the bone fixation elements 30 from withdrawing from the one or more bones 20 of the patient.

Figure 10:
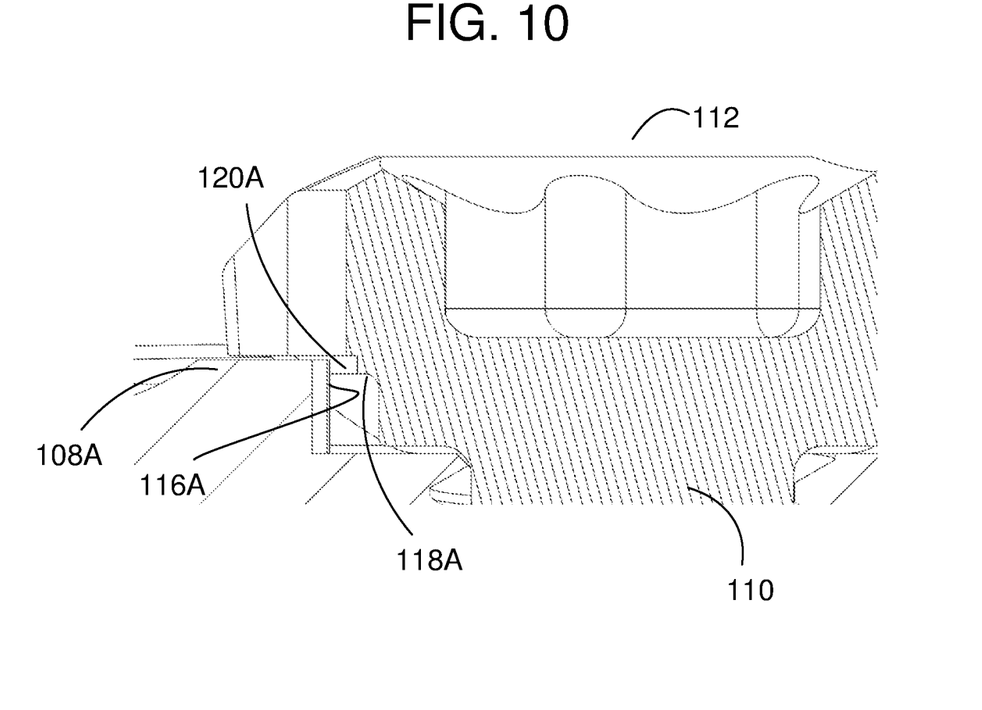
FIG. 10 is a side, cross sectional view of the retaining mechanism at a counter-rotational phase.
Figure 11:
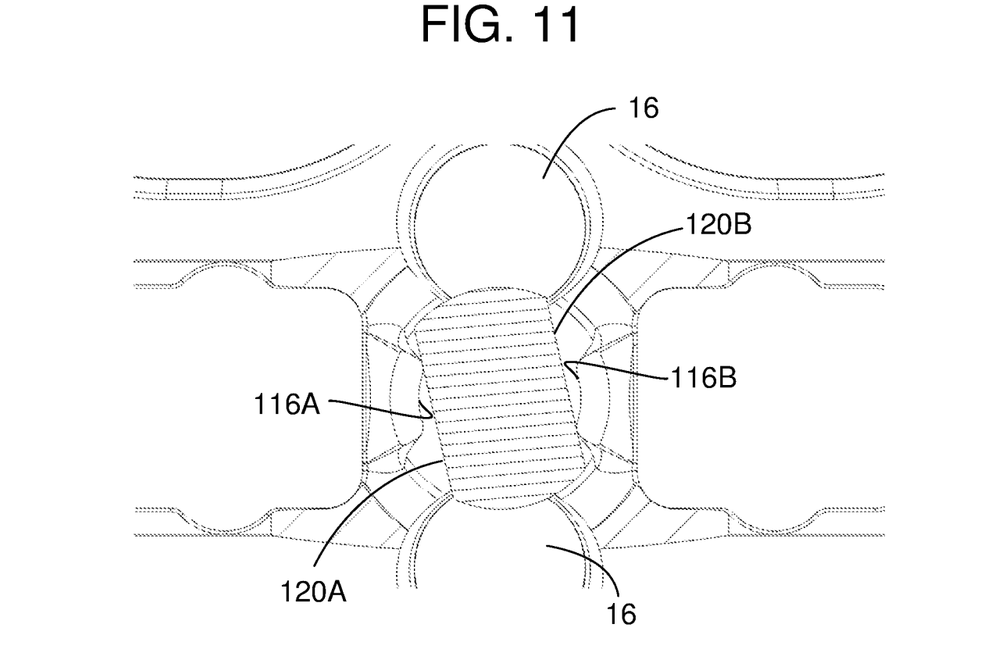
FIG. 11 is a top, cross sectional view of the retaining mechanism at the counter-rotational phase of FIG. 10.

After the blocker 104 is locked and the surgical procedure for implanting the orthopedic device 10 is completed, post-surgery pathological loads will be applied by the activities of the patient. These loads may result in the blocker 104 starting a counter-rotation (from the position shown in FIGS. 8-9 to or toward the position shown in FIGS. 10-11). Advantageously, such counter-rotation will not result in the portions of the head 112 unblocking the bone fixation elements 30 or permitting their withdrawal. Indeed, the subsequent counter-rotation of the blocker 104 results in the first and second opposing sidewalls 120A, 120B of the blocker 104 engaging the first and second sidewalls 116A, 116B of the first and second detent features 108A, 108B, thereby inhibiting further counter rotation of the blocker 104.

If there arises a desire to remove the orthopedic device 10 from the patient (i.e., unblocking the apertures 16 and withdrawing the bone fixation elements 30), such may be accomplished by applying a counter-rotational torque in excess of any such counter-rotational torques that would be applied in-situ. Indeed, a sufficient and significant subsequent counter-rotational torque applied to the blocker 104 will overcome the engagement of the first and second opposing sidewalls 120A, 120B of the blocker 104 and the first and second sidewalls 116A, 116B of the first and second detent features 108A, 108B. This is so due to the relative dimensions and orientations of the first and second opposing sidewalls 120A, 120B of the blocker 104 and the first and second sidewalls 116A, 116B of the first and second detent features 108A, 108B. Resultantly, there will be a reintroduction of rotation and sliding contact between the first and second contact surfaces 118A, 118B of the head 112 and the first and second upper surfaces 114A, 114B of the first and second detent features 108A, 108B. Further counter-rotation of the blocker 104 will drive the first and second contact surfaces 118A, 118B of the head 112 away and out of engagement with the first and second upper surfaces 114A, 114B of the first and second detent features 108A, 108B. Ultimately, the apertures 16 will become unblocked by the portions of the head 112 and withdrawal of the bone fixation elements 30 will be permitted.

Notably, the torsional loads required to unlock the blocker 104 from the feature 102 of the retaining mechanism 100 are much higher than those generated in-situ ensuring that the blocker 104 maintains a safe position overlying the bone fixation elements 30.

Figure 12:
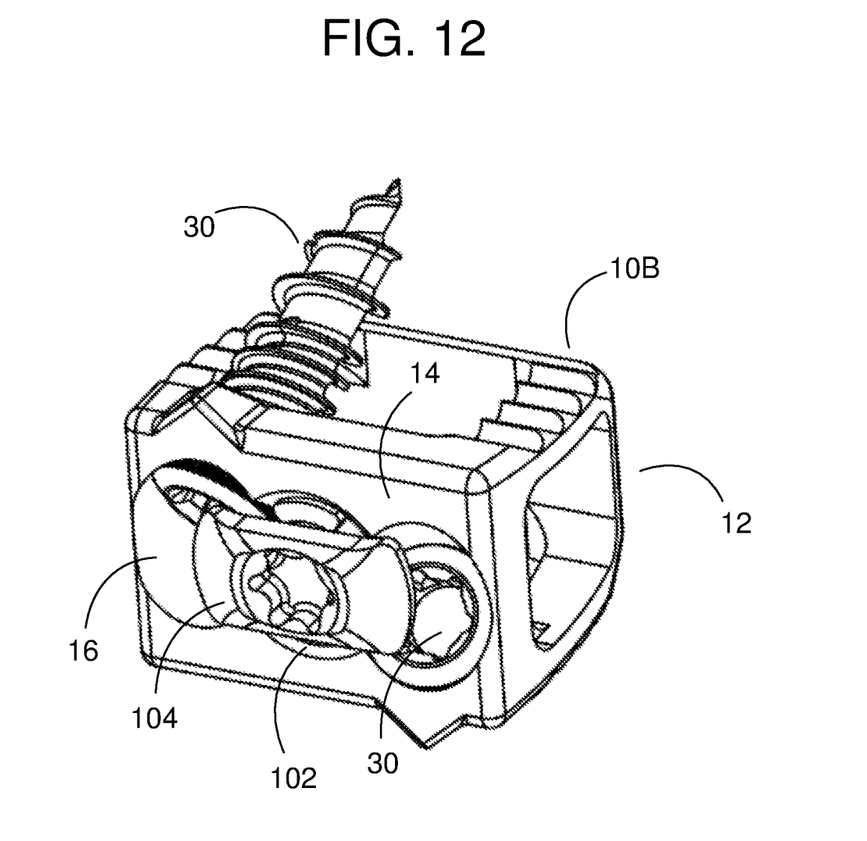
FIG. 12 is a perspective view of an alternative orthopedic device, i.e., a spinal cage, employing one of the retaining mechanisms.

FIG. 12 shows a perspective view of an alternative orthopedic device 10B, i.e., a spinal cage, employing a retaining mechanism 100 of substantially similar features as those discussed above. Accordingly, the above discussion of the retaining mechanism 100 applies with equal weight to the embodiment of FIG. 12.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. An orthopedic device, comprising:
    a base element having a primary surface, and a plurality of apertures extending from the primary surface through the base element, each of the apertures for receiving a respective bone fixation element that is configured to be driven into one or more bones of a patient in order to couple the orthopedic device to the patient; and
    a retaining mechanism operating to interrupt at least one of the bone fixation elements within at least one of the apertures from withdrawing from the one or more bones of the patient, the retaining mechanism comprising:
    a threaded bore extending from the primary surface into the base element, and being located adjacent to at least one of the apertures, the threaded bore defining an axis that is centrally located therethrough and extending from the base element,
    a detent feature disposed on, and extending outward from, the primary surface of the base element proximate to the threaded bore, and located adjacent to a periphery of the at least one of the apertures, the detent feature including: (i) a first detent feature disposed on, and extending outward from, the primary surface of the base element proximate to the threaded bore, and on one side of the axis, and (ii) a second detent feature disposed on, and extending outward from, the primary surface of the base element proximate to the threaded bore, and on an opposite side of the axis from, and in symmetry with, the first detent feature, and a blocker having a threaded shaft engaging the threaded bore, and a head at one end of the threaded shaft, wherein rotation of the blocker causes the head to overlie the at least one of the bone fixation elements within the at least one of the apertures such that the at least one bone fixation element is prevented from withdrawing from the one or more bones of the patient, and the rotation of the blocker by applying a rotational torque drives the head into engagement with the detent feature in such a way that: (i) in a locked rotational position of the blocker, abutting sidewalls of the detent feature and the head of the blocker prevent any further rotation and any counter-rotation of the blocker from the locked rotational position, and (ii) the counter rotation of the blocker sufficient to release the head from overlying the at least one bone fixation element is prevented until counter-rotational torque in excess of the rotational torque is applied.

2. The orthopedic device of claim 1, wherein the detent feature includes an upper surface spaced away from, directed away from, and oriented substantially parallel to, the primary surface of the base element.

3. The orthopedic device of claim 2, wherein the head of the blocker includes a contact surface oriented towards, and substantially parallel to, the primary surface of the base element.

4. The orthopedic device of claim 3, wherein rotation of the blocker drives the contact surface of the head of the blocker into engagement with the upper surface of the detent feature.

5. The orthopedic device of claim 3, wherein extension of the detent feature outward from the primary surface of the base element defines a first sidewall oriented transversely with respect to the primary surface of the base element, where the first sidewall is located adjacent to the periphery of the at least one of the apertures.

6. The orthopedic device of claim 5, wherein the head of the blocker includes an opposing sidewall oriented transversely with respect to the primary surface of the base element.

7. The orthopedic device of claim 6, wherein
initial rotation of the blocker drives the contact surface of the head of the blocker into engagement with the upper surface of the detent feature; and
further rotation of the blocker slides the contact surface rotationally across, and into tighter engagement with, the upper surface of the detent feature thereby taking up slack in the threaded shaft within the threaded bore.

8. The orthopedic device of claim 7, wherein further subsequent rotation of the blocker slides the contact surface off of the upper surface of the detent feature such that the first sidewall of the detent feature and the opposing sidewall of the blocker are oriented in opposition to one another.

9. The orthopedic device of claim 8, wherein the further subsequent rotation of the blocker results in a portion of the head of the blocker overlying the at least one of the apertures, thereby preventing the at least one of the bone fixation elements from withdrawing from the one or more bones of the patient.

10. The orthopedic device of claim 8, wherein still further subsequent rotation of the blocker is limited by the opposing relationship of, and engagement between, the first sidewall of the detent feature and the opposing sidewall of the blocker.

11. The orthopedic device of claim 8, wherein a subsequent counter-rotation of the blocker results in the opposing sidewall of the blocker engaging the first sidewall of the detent feature, thereby inhibiting further counter rotation of the blocker.

12. The orthopedic device of claim 11, wherein a sufficient and significant subsequent counter-rotation of the blocker to achieve the counter-rotational torque in excess of the rotational torque is applied will overcome the engagement of the opposing sidewall of the blocker and the first sidewall of the detent feature, thereby resulting in the reintroduction of rotation and sliding contact between the contact surface of the head and the upper surface of the detent feature.

13. The orthopedic device of claim 12, wherein a further counter-rotation of the blocker will drive the contact surface of the head away from and out of engagement with the upper surface of the detent feature, thereby unblocking the at least one of the apertures and permitting the at least one of the bone fixation elements to be withdrawn from the one or more bones of the patient.

14. The orthopedic device of claim 8, wherein:
the upper surface of the detent feature is defined as a first upper surface of the first detent feature;
the extension of the second detent feature outward from the primary surface of the base element defines a second sidewall oriented transversely with respect to the primary surface of the base element, and oppositely from the first sidewall;
the head of the blocker includes: (i) the contact surface, defined as a first contact surface, on one side of the threaded shaft, and oriented towards, and substantially parallel to, the primary surface of the base element, and (ii) a second contact surface, on an opposite side of the threaded shaft from the first contact surface, and oriented towards, and substantially parallel to, the primary surface of the base element; and
the rotation of the blocker drives the first contact surface of the head into engagement with the first upper surface of the first detent feature, and drives the second contact surface of the head into engagement with the second upper surface of the second detent feature.

15. The orthopedic device of claim 14, wherein:
the head of the blocker includes: (i) the opposing sidewall, defined as a first opposing sidewall, oriented transversely with respect to the primary surface of the base element, and being disposed on one side of the threaded shaft, and (ii) a second opposing sidewall, oriented transversely with respect to the primary surface of the base element, and being disposed on an opposite side of the threaded shaft from the first opposing sidewall;
further rotation of the blocker: (i) slides the first contact surface rotationally across, and into tighter engagement with, the first upper surface of the first detent feature, and (ii) slides the second contact surface rotationally across, and into tighter engagement with, the second upper surface of the second detent feature, thereby taking up slack in the threaded shaft within the threaded bore.

16. The orthopedic device of claim 15, wherein further subsequent rotation of the blocker:
(i) slides the first contact surface off of the first upper surface of the first detent feature such that the first sidewall of the first detent feature and the first opposing sidewall of the blocker are oriented in opposition to one another; and
(ii) slides the second contact surface off of the second upper surface of the second detent feature such that the second sidewall of the second detent feature and the second opposing sidewall of the blocker are oriented in opposition to one another,
wherein counter rotation of the blocker sufficient to release the head from overlying the at least one bone fixation element is inhibited.

17. The orthopedic device of claim 1, wherein the threaded bore is located adjacent to at least two of the apertures, and the head of the blocker is of a size sufficient to overlie at least two of the apertures and at least two of the bone fixation elements therein.

18. The orthopedic device of claim 1, wherein the orthopedic device is one of a spinal plate, and a spinal cage.

\* \* \* \* \*